United States Patent
Ladisch et al.

(10) Patent No.: US 10,093,951 B2
(45) Date of Patent: Oct. 9, 2018

(54) ENZYME CATALYZED DISASSEMBLY OF CORN KERNELS

(71) Applicant: Purdue Research Foundation, West Lafayette, IN (US)

(72) Inventors: Michael R. Ladisch, West Lafayette, IN (US); Youngmi Kim, Woodbury, MN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 14/511,723

(22) Filed: Oct. 10, 2014

(65) Prior Publication Data
US 2015/0024471 A1    Jan. 22, 2015

Related U.S. Application Data

(63) Continuation of application No. PCT/US2013/036397, filed on Apr. 12, 2013.

(60) Provisional application No. 61/623,365, filed on Apr. 12, 2012.

(51) Int. Cl.
C12P 19/02 (2006.01)
C08B 30/04 (2006.01)
C12P 19/04 (2006.01)

(52) U.S. Cl.
CPC ............ *C12P 19/04* (2013.01); *C08B 30/044* (2013.01)

(58) Field of Classification Search
None
See application file for complete search history.

(56) References Cited

U.S. PATENT DOCUMENTS

| 5,846,787 | A | 12/1998 | Ladisch et al. |
| 6,899,910 | B2 | 5/2005 | Johnston et al. |
| 7,452,425 | B1 | 11/2008 | Langhauser |
| 2003/0109011 | A1 | 6/2003 | Hood et al. |
| 2004/0028775 | A1 | 2/2004 | Olsen et al. |
| 2005/0244946 | A1* | 11/2005 | Hutchins ............... C12N 1/005 435/258.4 |
| 2007/0184159 | A1 | 8/2007 | Paustian et al. |
| 2008/0299256 | A1* | 12/2008 | Batie ................... C12N 9/2414 426/52 |

OTHER PUBLICATIONS

Hojilla-Evangelista, "Extraction and Functional Properties of Non-Zein Proteins in Corn Germ from Wet-Milling", Journal of the American Oil Chemists' Society 2012 (e-Pub: Jul. 2011), vol. 89, pp. 167-174.*
Voorhees, "Coarse grinding: An equipment overview", Powder and Bulk Engineering Jun. 2010, pp. 1-4.*
Lamsal et al., "Effect of corn preparation methods on dry-grind ethanol production by granular starch hydrolysis and partitioning of spent beer solids", Bioresource Technology 2011, vol. 102, pp. 6680-6686.*
Borras et al., "Control of kernel weight and kernel water relations by post-flowering source-sink ratio in maize", Annals of Botany 2003, vol. 91, pp. 857-867.*
Moliner et al., "Tin-containing zeolites are highly active catalysts for the isomerization of glucose in water", PNAS 2010, vol. 107, pp. 6164-6168.*
International Search Report and Written Opinion, dated Jul. 15, 2013.
Kim, Youngmi et al. 'Enzyme catalyzed disassembly of corn kernels.' In: CUT C Conference, Indiana Corn Growers, Indianapolis, IN, Jun. 4-6, 2012. See the whole document.

* cited by examiner

*Primary Examiner* — Michelle F Paguio Frising
(74) *Attorney, Agent, or Firm* — Woodard, Emhardt, Moriarty, McNett & Henry, LLP

(57) ABSTRACT

Whole corn kernels or particles thereof are enzymatically disassembled. The method can produce a solid starch fraction, a solid pericarp fraction, and a liquid fraction. A high purity starch solids product can be provided suitable for use as a feedstock in other chemical processes.

34 Claims, 6 Drawing Sheets

ENZYME CATALYZED DISASSEMBLY OF CORN KERNELS

CROSS REFERENCE TO RELATED APPLICATIONS

This application is a continuation of and claims the benefit of priority of International Application Serial No. PCT/US2013/036397, filed Apr. 12, 2013, which claims the benefit of priority of U.S. Provisional Patent Application No. 61/623,365 filed Apr. 12, 2012, each of which is hereby incorporated herein by reference in its entirety.

BACKGROUND

Due to the capital- and energy-intensive nature of petroleum refineries and the greenhouse emissions they cause, biorefineries based upon renewable feedstocks are becoming more attractive. They offer potential for sustainable manufacturing of fuels and chemicals with reduced cost, energy and carbon footprint.

One of the main goals of biorefineries is to produce energy from renewable domestic raw materials to displace imported petroleum. Corn biorefineries, for example, dry mills, that currently produce ethanol and animal feed, are expected to seek diversified product portfolios as ethanol subsidies are phased out. Incorporating a variety of fuels and chemicals into a biorefinery's product portfolio is expected to be crucial to facilitate expansion of the biorefinery industry, maximize profit and make the biorefineries economically viable. Corn biorefineries with diversified product portfolios offer great potential for corn farmers and sugar producers to capture added value, and a higher return on investment, while achieving energy and economic goals simultaneously. Also, depending on the type of product targeted, this could enhance the energetics of the corn biorefinery so that life cycle analysis could show that these biorefineries would possibly fit the definition of advanced biofuels, for example, by providing a 50% reduction in greenhouse gas emissions.

Sugars such as glucose may be used as feedstock for production of renewable hydrogen, they may also be dehydrated to furfurals or levulinic acid to enable production of gasoline, jet, and diesel fuel hydrocarbons. Several important platform chemicals that can be produced from sugars include furfural, hydroxymethylfurfural (HMF), levulinic acid, and γ-valerolactone, all of which may add significant value to the existing corn biorefineries through product diversification while reducing risk and increasing revenue and profits from corn.

In light of this background, there remain needs for improved and/or alternative methods for processing feedstocks in the field of biorefining.

SUMMARY

In certain aspects, the present invention provides methods for processing corn products The methods include enzymatically digesting corn kernels in whole or essentially whole form or in a particulate form (the latter hereinafter sometimes referred to as "corn kernel particles") in a digestion medium to form a solid corn starch fraction, a solid pericarp fraction, and a liquid fraction containing dissolved glucose. The methods may also include separating the solid corn starch fraction, the solid pericarp fraction and the liquid fraction. The separating step or steps may be performed using a physical separation technique such as filtration, centrifugation, centrifugal filtration, settling, screening, flotation, or any other appropriate method. Corn kernel particles for charging to the enzymatic deconstruction step can be formed by suitable methods. This may be accomplished for example by cutting, degermination, cracking, fracturing, miffing, or any other suitable means for forming corn kernel particles. The corn kernel particles can be formed in a dry milling process that may also serve to degerminate the corn. Corn kernel particles can be formed with a moisture content of the starting corn kernels of less than about 30%. The number of corn kernel particles formed may number from about two to about twenty particles per starting material corn kernel.

In other aspects, the invention provides an enzyme composition suitable for enzymatically deconstructing corn kernel material. The composition includes at least a pectinase, a cellulase, and a β-glucosidase.

Additional embodiments of the invention, as well as features and advantages thereof, will be apparent from the descriptions herein.

DETAILED DESCRIPTION

Figure 1:
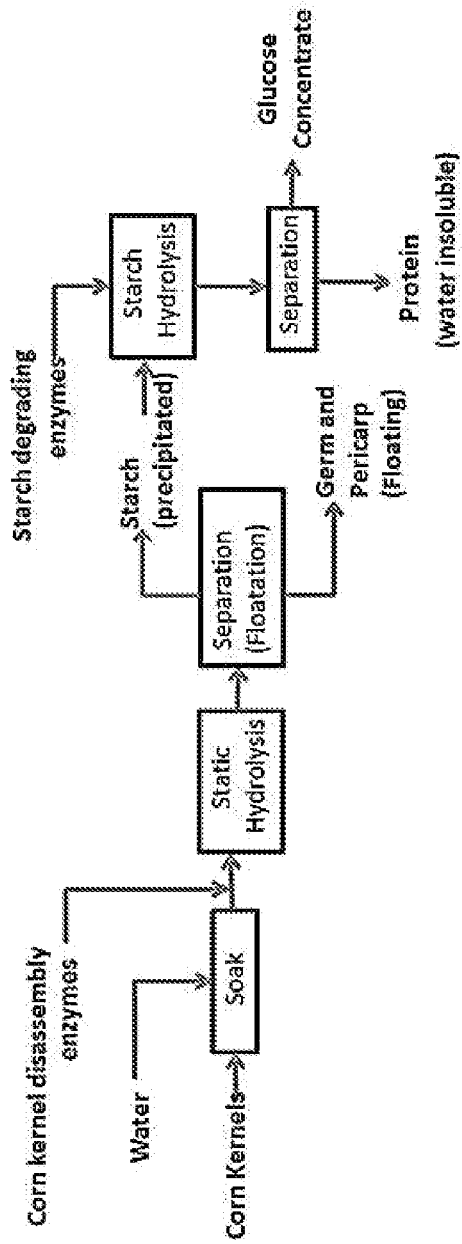
FIG. 1 is a block flow diagram of one embodiment of a corn processing method.

For the purposes of promoting an understanding of the principles of the invention, reference will now be made to certain embodiments and specific language will be used to describe the same. It will nevertheless be understood that no limitation of the scope of the invention is thereby intended, such alterations and further modifications, and such further applications of the principles of the invention as described herein being contemplated as would normally occur to one skilled in the art to which the invention relates.

As disclosed above, certain aspects of the present disclosure relate to corn processing. Corn kernels, including whole kernels and/or particles thereof, are processed to achieve an enzymatic deconstruction and separation of component parts of the corn kernel, which can include for example separation of starch and pericarp fractions, and potentially also germ fractions when germ is present.

Corn kernel starting materials suitable for use in the processes of the present disclosure include yellow dent corn kernels are used, although other varieties of corn kernels may also be used. The whole kernels as starting materials can be processed so as to increase the surface area of the corn kernels available to enzymes. This processing can form particles from the corn kernels by any suitable means, which may include for example cutting, crushing, cracking, fracturing or other techniques, which may be conducted as dry milling operations. Additionally or alternatively, this processing can disrupt the pericarp of the kernels, facilitating access of an enzyme-containing medium and/or another processing media to the interior of the kernels. Illustratively, the kernel pericarp (hull material) can be disrupted by removal of the tip caps of starting corn kernels while nonetheless leaving the kernels as whole or essentially whole kernels. The formed whole corn kernels or corn kernel particles to be subjected to enzymatic digestion can include at least attached pericarp and endosperm from the corn kernels. The processing to form such whole corn kernels or corn kernel particles for the digestion can be conducted while the corn kernels of the starting corn product have a relatively low moisture content, for example less than about 30% moisture by weight, and in certain embodiments in the range of about 10% to about 30% moisture by weight. In one illustrative embodiment, the tip cap can be removed from such starting corn kernels by separating (e.g. cutting) the tip cap from the pericarp. In another embodiment, the starting corn kernels can be cracked. In still another embodiment, the corn kernels can be subjected to degermination, for example in a degermination apparatus, in order to remove the germ from the corn kernels and form particles including attached pericarp and endosperm. This degermination or other pre-processing to provide a corn kernel particulate is desirably conducted as a dry milling operation.

Corn kernel particles charged to enzymatic digestion according to this disclosure can have relatively large particle sizes. For these purposes, in processing to particles, the corn kernels can be fractionated into between, on average, 2 to 20 corn kernel particles per corn kernel, each having a weight from about 0.02 g to about 0.4 g. More preferably, the corn kernels are fractured into between, on average, 2 to 10 corn kernel particles per corn kernel, each having a weight from about 0.02 g to about 0.4 g. Additionally or alternatively, the corn kernel particles can have an average maximum particle dimension in the range of about 3 mm to about 20 mm. It will be understood that such particulate-forming processes may also produce some fines or other smaller particles, which may be separated from the larger particles or which may also be charged to the enzymatic digestion processing. In some aspects, starting corn kernels may be degerminated before fractionation into the corn kernel particles to be enzymatically digested. Alternatively, the starting corn kernels may be degerminated in conjunction with fractionating the kernels into particles, and the germ may optionally be separated before charging the material to the enzymatic digestion. It will be understood by those skilled in the pertinent field that degermination of corn kernels, and separation of the germ, can nonetheless leave some residue of germ mixed with or attached to the corn kernel particulate to be charged to enzymatic processing. In preferred aspects where the germ is separated from other kernel particles to be subjected to enzymatic processing, the degree of degermination will be at least about 90% (i.e. at least about 90% of the germ in the original kernels will have been separated, and thus no more than about 10% of the germ in the original kernels will be included in the kernel particles charged to the enzymatic digestion). However, higher or lower degrees of degermination may be used in other aspects of the present invention.

Figure 4:
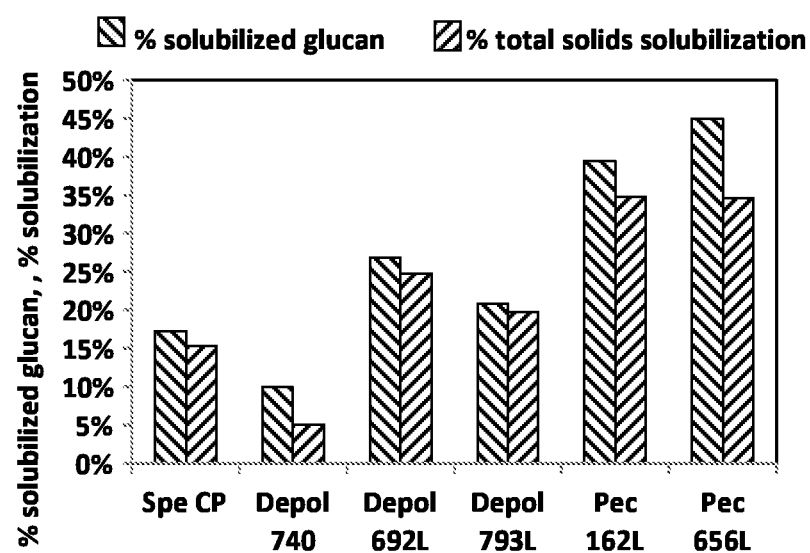
FIG. 4 shows percent glucan (cellulose and starch) solubilized and percent total solids solubilization of corn kernels hydrolyzed by different commercial enzyme preparations. 15% w/v dry corn kernel (tip cap removed) loading, 5% v/v enzyme loading, pH about 5.0 citrate buffer, 50° C., 1 week, 200 rpm.

As disclosed above, processes herein involve an enzymatic digestion or disassembly of corn kernel materials. Enzymes suitable in the processes of the present invention include, but are not limited to, cellulases, β-glycosidases, xylanases, β-xylosidases, pectinases, α-amylases, α-arabinofuranosideases, ferulic acid esterases, and p-coumaryl esterases. One or more enzymes may be used in any quantity and any ratio suitable for processes of the present invention. For example, commercial formulations of enzymes may be used in embodiments of the present invention. Suitable commercial formulations of enzymes for use in processes of the present invention include, but are not limited to, Spezyme CP, Depol 740L, Depol 692L, Depol 793L, Pectinase 162L, and/or Pectinase 656L. In one embodiment, one or more commercial mixtures of enzymes are employed to enzymatically digest corn kernels or corn kernel particles. In one monument, the concentration of at least one enzyme is at least about 0.5% v/v. In one embodiment, one or more enzymes are present and the concentration of between about 0.2% v/v to about 10% v/v. In another embodiment, a mixture of three commercially available enzyme solutions was used in the processes of the present invention. For example, in one illustrative example, Pectinase 162L was present at 2% (v/v), Depol 793L was present at 0.5% (v/v), and Spezyme CP was present at 0.5% (v/v) in an aqueous citrate buffer at about pH 5.5 for 2 weeks at 45° C. agitating at 100 rpm. Known screening techniques may be used in determining the activity of candidate enzymes for use in the enzymatic digestion. For example, with reference to FIG. 4, shown is a bar graph of the percent solubilization of glucan and other solids using different enzymes which were screened for potential use in processes herein. It will be understood that similar screening can be used in conjunction with other enzyme candidates.

The enzymatic digestion can be conducted effectively to separate attached endosperm (starch) and pericarp (hull) components of the corn kernels or corn kernel particles subjected to the digestion, to form separate solid starch and pericarp fractions. During enzymatic digestion, in some embodiments, at least a portion of the starch in the kernels or kernel particles is also hydrolyzed to form glucose, which can be solubilized in the digestion medium. As well, if the germ from the starting material corn kernels, or at least a portion of such germ, is present in the enzymatic digestion, the digestion can effectively separate the germ as a solid (which can float in the digestion medium) and/or as oil that is suspended or solubilized in the digestion medium.

Digestion mediums used in embodiments of the present invention will typically be aqueous mediums. Such aqueous mediums may be buffered to a desired pH or pH range at which the enzymes are active. For example, the pH of the digestion medium can be in the range of about 5 to about 8, more typically in the range of about 5 to about 7. In some embodiments, a citrate buffer or other buffer can be used to buffer the digestion medium to a pH of about 5.5.

The corn to water ratio in an aqueous digestion medium can be any suitable ratio for use in the enzymatic digestion. In certain forms, the corn (kernel or kernel particles) to water ratio is from about 1% w/v to about 30% w/v (i.e., the weight of the corn divided by the weight of the water with which it is combined equals about 0.01 to 0.3), more preferably about 5% w/v to about 30% w/v, and even more preferably about 15% w/v to about 30% w/v. In a more specific embodiment, the ratio of corn to water in the digestion medium can be from about 25% w/v to about 30% w/v.

The enzymatic digestion medium can be contacted with the corn kernels or corn kernel particles for any suitable amount of time to achieve the desired digestion or disassembly. In certain aspects, this contact time can be from about one hour to about two weeks, or from about one hour to about two days, or from about one hour to about one day. The contact time selected can be dependent upon a number of other factors including for example the temperature of the digestion, the concentration and/or activity of the enzyme(s) used, and the extent of disassembly of the kernels or kernel particles desired before further processing. Likewise, the selection of these other conditions can be dependent upon each other, and upon the desired contact time for the enzymatic digestion.

In regard to temperatures during the enzymatic digestion, any appropriate temperature at which the enzyme(s) is/are active may be used. In some embodiments, the temperature of the enzymatic digestion medium during the digestion is in the range of about 10° C. to about 65° C., or about 20° C. to about 65° C., or about 30° C. to about 65°. In one specific preferred aspect, the temperature of the enzymatic digestion medium during the digestion is in the range of about 40° C. to about 60° C.

Figure 5:
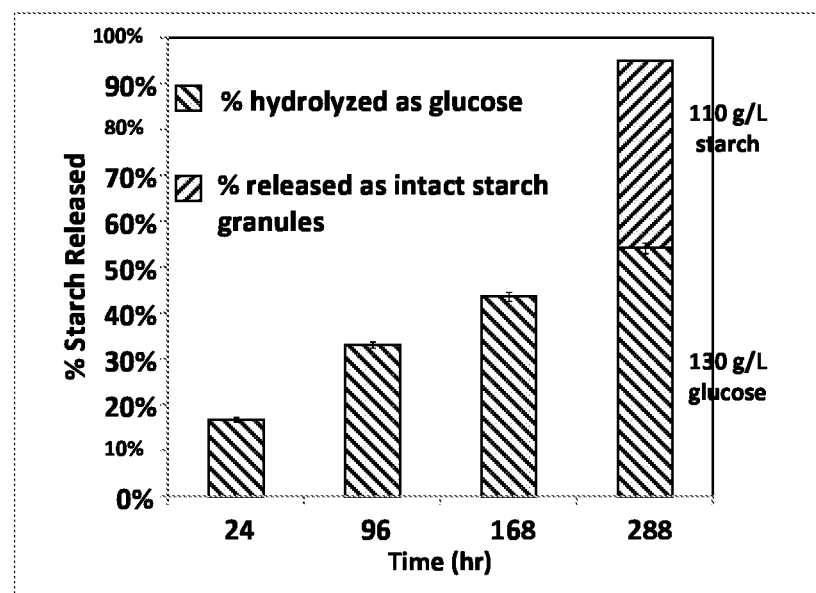
FIG. 5 shows the amount of starch released during enzymatic deconstruction of corn kernels. The experiment was performed using 30% w/v corn kernel with tip cap removed in an aqueous slurry, Pectinase 162L at 2% v/v, Depol 793L at 0.5% v/v, and Spezyme CP at 0.5% v/v, pH about 5.5 citrate buffer, 45° C., 2 weeks, 100 rpm.

FIG. 5 provides a bar graph resultant of one experimental run of an illustrative enzymatic digestion under selected conditions of enzymes, temperature, and contact time. In particular, shown is the percent of starch released over time in the run. In this run, corn kernels with their tip cap removed were incubated in an aqueous digestion medium at a concentration of 30% w/v. The digestion medium was buffered to about pH 5.5 with citrate buffer, and contained 2% v/v Pectinase 162L, 0.5% Depol 793L, and 0.5% Spezyme CP. The medium was allowed to react at 45° C. for two weeks with 100 revolutions per minute of a mechanical mixer. After 24 hours only a small fraction of starch had been released. After 288 hours almost all of the starch from the corn kernels had been released.

The enzymatic digestion can be conducted in any suitable reaction vessel. Suitable vessels include but are not limited to tank vessels, pipe or tubular reactors, continuously stirred tank reactors, plug flow reactors, semi-batch reactors, or other suitable vessels. During the enzymatic digestion, in one mode of operation, the digestion medium containing the corn material is not agitated. In other modes, during the digestion, the digestion medium containing the corn material can be agitated. Any suitable means of agitation can be employed. Preferably, however, any agitation used is at a low level insufficient to achieve disassembly of the corn kernels or corn kernel particles on its own, but sufficient to facilitate contact of the enzyme(s) in the medium with the corn material. In doing so, the agitation can also stir or otherwise move the corn kernels or corn kernel particles within the digestion medium. In a reaction vessel in which separation of solid starch and solid pericarp (and potentially also solid germ if present) fractions is achieved under gravity sedimentation conditions, this agitation can also facilitate freeing the disassembled solid materials from their mixture with one another so that the solid starch can settle to or toward the bottom of the vessel and the solid pericarp (and potentially also solid germ) can float to or toward the top of the vessel. Agitation, when used, can be achieved for example with a mechanical mixer such as a dispersion blade, a static mixer, or a rotating blade mixer. Such a mechanical mixer may be powered by electric, hydraulic, pneumatic, or other suitable means. In other embodiments, the digestion medium can be agitated during the enzymatic digestion by the inflow and/or outflow of liquid of the digestion medium, including for example by flow of the liquid through a circulation loop. Such a circulation loop may include one or more openings into the vessel from which circulated liquid is forced sufficiently to agitate the digestion medium, including in the manners discussed above. In desired aspects, the one or more openings into the vessel are at or proximate to the bottom of the reaction vessel and the circulated liquid is forced upflow through solids in the digestion medium.

The enzymatic digestion can be conducted so as to result in a digested medium containing a solid corn starch fraction (e.g. in the form of starch granules released from the kernels or kernel particles), a solid pericarp fraction (fibrous fraction), and a liquid fraction containing dissolved glucose. The liquid of the digestion medium, preferably aqueous liquid, can be of sufficient volume to provide a stratified material in the reaction vessel in which a solid corn starch enriched fraction is at the bottom, a solid pericarp enriched fraction resides above the solid corn starch enriched fraction, and a liquid fraction with dissolved glucose resides above the solid pericarp enriched fraction. When agitation is employed, under appropriate conditions, such a stratified material may form even while agitation is applied; or, such a stratified material may form upon the cessation of agitation. The use of kernels or relatively large kernel particles, for example having sizes as specified above, facilitates an efficient separation of the solid corn starch and the solid pericarp. The solid pericarp fragments (fiber material) resultant of the enzymatic digestion are also large and thus are more readily separated in the liquid digestion medium from the starch, even with no or low levels of agitation as discussed above. The solid pericarp fragments desirably have an average maximum cross-sectional dimension that is greater than that of the solid starch granules or other solid starch particles formed by the enzymatic digestion. When germ is present in the corn material charged to the digestion, solid germ will typically float to the top of the digestion medium and remain there until the completion of the digestion, unless prior removed. As well, other kernel fragments such as pericarp fragments that have attached germ can float to the top of the digestion medium and remain there until the completion of the digestion, unless prior removed.

In certain aspects, at the completion of the enzymatic digestion, the solid starch product liberated during the digestion can constitute at least about 20% by weight of the original total starch in corn kernels or corn kernel particles charged to the enzymatic digestion, for example in certain modes from about 20% to about 70%. It will be understood that these amounts are dependent upon starting materials used and conditions of the enzymatic digestion, and may vary from these ranges in other embodiments. Likewise, it will be understood that in certain modes of operation, the liberated solid starch may be collected from the reaction vessel, for example periodically, as it is formed, while in other modes of operation the liberated solid starch will be allowed to collect in the vessel throughout the digestion, for collection after completion of the digestion.

At the completion of the enzymatic digestion, the solid pericarp product liberated during the digestion can constitute at least about 20% by weight of the original total pericarp in the corn kernels or corn kernel particles charged to the digestion, and in certain aspects in the range of about 20% to 99% or essentially 100% of the original total pericarp content of the corn kernel or corn kernel particles charged to the enzymatic digestion. In certain modes of operation, the liberated pericarp may be collected from the reaction vessel, for example periodically, as it is formed, while in other modes of operation the liberated pericarp will be allowed to collect in the vessel throughout the digestion, for collection after completion of the digestion.

In some operative modes, the enzymatic digestion will also result in the formation of a solid corn germ fraction. It will be understood that when a degerminated corn material is charged to the enzymatic digestion, this may be only a very minor fraction, whereas when a non-degerminated corn material is charged to the enzymatic digestion, this may be a more significant fraction. Also, the conditions of the enzymatic digestion may result in the conversion of some or all of any germ fraction present into oil that may be solubilized and/or suspended in the digestion medium.

As disclosed above, the enzymatic digestion may also result in the presence of dissolved glucose in the aqueous solution resultant of hydrolysis of a portion of the starch component of the corn kernels or kernel particles. In this regard, the glucose in the digested medium can include glucose resultant of hydrolysis of up to about 80% by weight of the total original starch content in the corn kernel or corn kernel particles subjected to the enzymatic digestion, and in certain aspects hydrolysis of about 30% to about 70% by weight of such total original starch content. In additional or alternative features, the dissolved glucose concentration of the enzymatically digested medium can range from about 1 g/L to about 140 g/L.

Fractions formed during the enzymatic digestion can be separated from one another by any suitable means and in any suitable order or combination. For example, in some inventive variants, a solid corn starch fraction, a solid pericarp fraction, and a liquid fraction containing dissolved glucose are separated from one another. Separations herein may be achieved for example using gravity settling or sedimentation, centrifugation, flotation, filtration, or centrifugal filtration, or combinations thereof. The separation(s) can result in an isolated solid pericarp fraction, an isolated liquid fraction containing dissolved glucose, and an isolated solid starch fraction. In one mode of operation, a first, solid pericarp product is first separated from a second product including the solid starch fraction and the liquid fraction containing dissolved glucose. The second product, in some forms, can the be processed (e.g. by centrifugation or otherwise) to separate the solid starch fraction and the liquid fraction containing dissolved glucose, which can be separately recovered as isolated fractions. In other forms, the second product can be subjected to digestion (e.g. with a suitable enzyme as identified herein) to hydrolyze the solid starch to additional glucose, and the resultant glucose solution can be used in further fermentation or chemical synthesis processes, including any of those described herein for glucose products. These and other variations on the overall separation and use of fractions from the enzymatic deconstruction of the corn kernel materials will be apparent from the descriptions herein.

Each of the isolated fractions can be further processed. For example, the solid starch fraction can be further purified by washing (e.g. with water or another wash liquid) or other means. The solid starch fraction may also be dried before and/or after any further purification of the fraction by any means, including for example air drying or heated drying. In preferred processes, an isolated solid starch fraction is formed that is constituted at least 80% by weight of starch, more preferably at least about 85%, and even more preferably at least about 90%. Similarly, the isolated solid pericarp fraction may also be further purified by any suitable means, for example by washing.

In one aspect of the present disclosure, the isolated solid starch fraction can be enzymatically or otherwise converted to glucose. Any method for converting starch to glucose may be used. Suitable methods include, but are not limited to, enzymatic or acid hydrolysis methods. Illustratively, an amylase enzyme can be used to convert the isolated starch fraction into glucose. The glucose produced from starch may be utilized in downstream processes including but not limited to, fermentation (e.g. for conversion to alcohols such as ethanol), as well as conversion into other chemicals such as, but not limited to, levulinic acid, hydroxyl methylfurfural, furfural, and γ-valerolactone. These conversions may be carried out by reacting the glucose in the presence of catalysts such as acid catalysts, basic catalysts, solid catalysts, metal catalysts such as transition metal catalysts including but not limited to solid metal catalysts such as platinum, palladium, copper, solid supported catalysts, zeolites, heterogeneous catalyst, and homogenous catalysts. This reaction can form a chemical product other than glucose.

Similarly, the dissolved glucose in the liquid of the digestion medium may also be used in downstream processes. Such downstream processes include, but are not limited to, fermentation, for example, to ethanol, as well as conversion into other chemicals such as, but not limited to, levulinic acid, hydroxyl methylfurfural, furfural, and γ-valerolactone. These transformations may be carried out by catalysts such as those identified hereinabove.

An isolated solid pericarp fraction can also be used in downstream processes or products. For example, fiber from the solid pericarp fraction may be used as feedstock or for the production of such end products as corn fiber gum and corn fiber oil.

In processes in which the enzymatic digestion yields a solid corn germ fraction, any suitable means for separating the corn germ fraction from other fractions such as the solid corn starch fraction, the solid pericarp fraction, and/or a glucose containing liquid may be employed. These include for example settling, centrifugation, flotation, filtration, or centrifugal filtration.

Referring now to FIG. 1, provided is a simplified block diagram of one embodiment of the present invention. Initially whole corn kernels (tip cap-removed or not) or corn kernel particulates are dispersed and soaked in water. One or more enzymes are then added to the solution where static hydrolysis occurs. A solid corn starch fraction, a solid pericarp fraction, and a liquid fraction containing dissolved glucose are formed. The germ and pericarp float at the top of this solution and may be isolated for use in further processes. The solid starch precipitate may be isolated and purified. Additional starch degrading enzymes may be added to this purified starch solid to produce glucose as well as other proteins.

Figure 2:
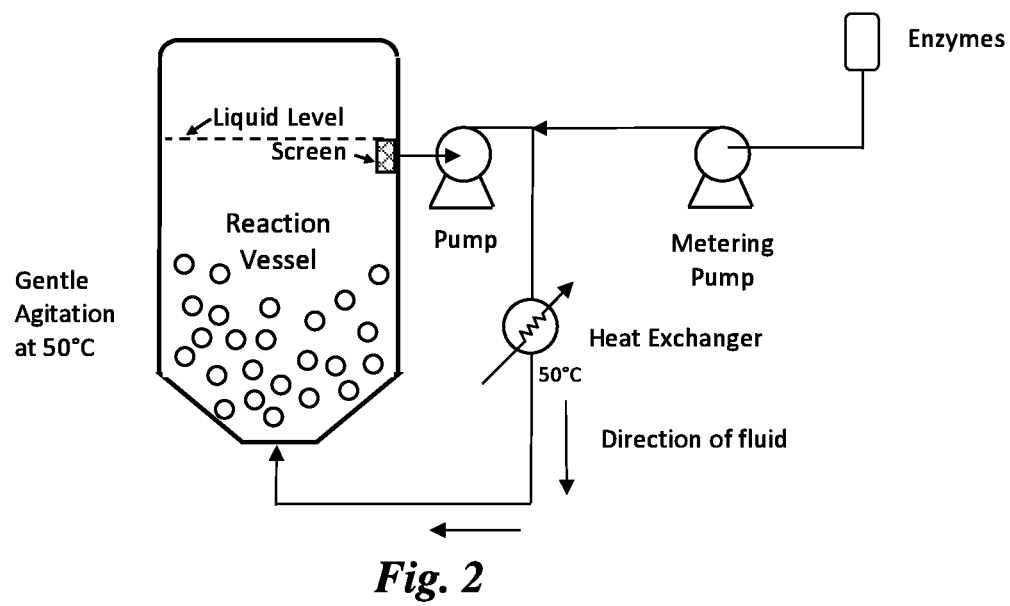
FIG. 2 is a schematic diagram of one embodiment of the present disclosure with liquid flow to affect gentle agitation.
Figure 3:
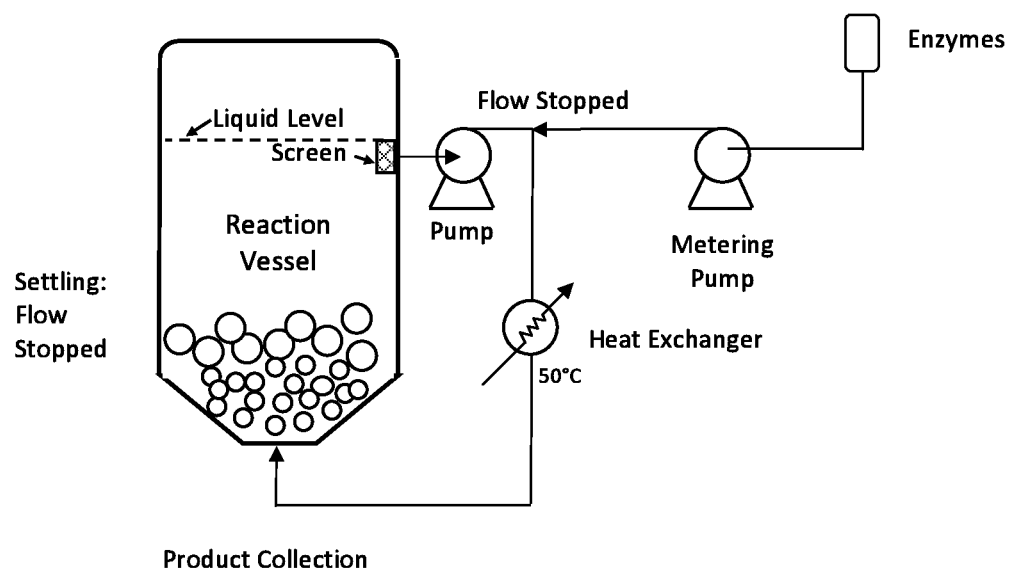
FIG. 3 is a schematic diagram of one embodiment of the present disclosure as in FIG. 2 with the liquid flow stopped to allow for settling of particulate matter such as pericarp and starch.

As discussed above, certain modes of operation of the enzymatic digestion can involve agitation of vessel contents during the digestion by circulation of amounts of the liquid of the digestion medium through a circulation loop in a fashion that agitates solids of the medium. FIG. 2 provides a diagram of one system for conducting an exemplary such process. A reaction vessel is provided and is filled partially with the digestion medium. A circulation loop is established including a screen or filter for liquid outflow from the vessel (to retain the corn solids in the vessel), a pump, a heat exchanger, and an inflow opening into the bottom of the reaction vessel. The pump circulates the liquid through the circulation loop, and the heat exchanger heats the liquid in the loop to a desire temperature, for example 50° C. As shown, the system can also include a source of an enzyme(s)-containing liquid medium, and a pump for metering the enzyme(s)-containing liquid medium into the circulation loop, for example at the beginning of the enzymatic digestion and/or periodically or continuously during the enzymatic digestion. It will be understood that one or more valves can be provided, as desired, to enable selective interruption of flow within the circulation loop and/or from the source of enzyme(s)-containing solution into the circulation loop. FIG. 3 shows the system of FIG. 2 where flow within the circulation loop has been stopped and a solid corn starch fraction, a solid pericarp fraction, and a liquid fraction containing dissolved glucose are formed. These fractions may then be separated and potentially purified as discussed herein.

Disclosure of Certain Exemplary Embodiments and Product Uses

With reference to one particular illustrative aspect, a new approach for disassembly rather than destruction of corn kernels into its components (starch, pericarp, and germ) by enzyme catalysis at temperatures of 50° to 60° C. (FIG. 1) is presented. The enzymes are formulated to separate pericarp from endosperm while leaving germ floating on the reaction solution at the end of the process. The process involves no mechanical grinding and no chemical steeping of corn kernels prior to the enzymatic deconstruction and can be easily adapted to a conventional dry grind process. Fractionation of pericarp and germ, followed by washing will generate a starch stream which is subsequently hydrolyzed to glucose by amylases.

In another aspect of the instant exemplary embodiments disclosure, capturing concentrated glucose and other sugars from corn for the purposes of synthesizing chemical building blocks is disclosed. Intermediate chemicals and the polymers derived from them are valued at over $2 trillion, and could provide a chemical source that is both renewable and derived from crops grown in the United States, for example, including but not limited to corn. While the value of the market is large, the total amount of corn that would be consumed by the production of chemicals as compared to ethanol would be small and would have little impact on food production. In order to achieve chemical conversion, highly concentrated and substantially pure sugars are needed, and the sugars should have a low cost in order to maximize the margins that are derived by adding value through chemical synthetic pathways.

The current exemplary embodiments disclosure describes a novel process and contains a non-limiting list of embodiments including enzyme directed deconstruction of corn kernels so that a solid starch precipitate results. Corn kernels contain approximately 72% starch, about 5-6% hemicellulose, 2.4% cellulose and soluble sugars, lipids, proteins, and ash. In the instant exemplary embodiments disclosure, a method for the fractionation of corn kernels into intact germ, starch, sugar, and pericarp fractions is disclosed. The method involves removing the tip cap, placing the dried corn kernels at 12% moisture in a 30% weight/volume slurry in water, and then adding a mixture of enzymes: a pectinase for example pectinase 162 L, a cellulase for example Spezyme CP, and a β-glucosidase for example Novozyme 188. The natural pH at which this mixture is buffered is about 5.5. Incubation of the mixture at 45° C. for 2 weeks, under gentle stirring, results in clean fractionation of the starch from the germ and from the pericarp. Facile separation is then achieved and the germ floats, the starch goes to the bottom of the vessel, and the pericarp also floats. Relative to current practices, mechanical inputs are minimal and have low energy. The pericarp, being intact, can then be further processed to cellulosic ethanol, for example, using other technology known by person having ordinary skill in the art.

The application of this technology would be principally in the corn dry milling industry, which is currently producing corn from ethanol. As cellulose plants come on-line, and the corn subsidy is reduced, the amount of ethanol that can be derived from corn, in an economic manner, is likely to decrease over the coming 5 years. In this context, having value added products derived from corn in these facilities would in fact enhance margins and improve markets for corn, and at the same time, providing a greater revenue stream, would not significantly increase, and possibly decrease, the corn being diverted from food and feed use into ethanol and chemical production. The materials that are obtained are directly suitable for production into chemical building blocks for polymers. At least one embodiment of the instant disclosure is related to the combination of conditions using a static system which does not require the corn to be ground up or size-reduced. In another embodiment, gentle agitation is used periodically or continuously. By maintaining the natural structure of the corn kernel, and using enzymes and aqueous processing at temperatures of 45° C., the kernel may be fractionated into value added components, thereby adding margin to products that could be derived from the corn kernel.

EXPERIMENTAL

For the purpose of promoting a further understanding of aspects of the present disclosure and features and advantages thereof, the following specific Experimental is provided. It will be understood that this Experimental is illustrative, and not limiting, in nature.

Example 1

Enzymatic Digestion of Corn Kernels

Materials and Methods:
Yellow dent corn kernels (12% moisture) were used. Commercial enzymes, Depol 692L, Depol 740L, Depol 793L, Pectinase 162L, Pectinase 656L were purchased from Biocatalysts Ltd (Wales, UK). Spezyme CP was provided by Dupont (previously Genencor). All other chemicals were purchased from Sigma-Aldrich.

Enzyme Activity Measurements.
Cellulase and cellobiase activities were measured by procedures of the International Union of Pure and Applied Chemistry (IUPAC). All other enzyme activities were measured by following the procedures below.

Endoglucanase (CMCase):
One unit of CMCase activity is defined as the amount of enzyme that releases 1 µmol of glucose per min.
1) 200 µl enzyme+1.8 ml of 1% CMC
2) Incubate for 30 min at 50° C.
3) Stop the reaction by boiling at 95° C. for 5 min
4) Glucose liberated during the reaction was measured by HPLC.

Xylanase:
  One unit of xylanase activity is defined as the amount of enzyme that produces 1 µmol of xylose per min.
  1) Add 100 µl enzyme+400 µl of 1% (w/w) OSX
  2) Incubate for 10 min at 50° C.
  3) Stop reaction by adding 2 ml DNS and boil for 5 min
  4) Read ABS at 540 nm.

β-Xylosidase:
  Hydrolysis of pNP-substrate is determined by the release of p-nitrophenol and the optical density was measured at 410 nm. One enzyme unit is defined as the amount of enzyme releasing 1 µmol of p-nitrophenol per min.
  1) 100 µl of enzyme+400 µl of 10 mM nitrophenyl xylopyranoside
  2) Incubate for 15 min at 50° C.
  3) 1 ml of cold 1M sodium carbonate was added to stop the reaction
  4) Measure absorbance at 410 nm.

Pectinase (Polygalacturonase):
  Polygalacturonase activity was measured by determining the amount of galacturonic acid released from polygalacturonic acid. One unit is defined as the amount of enzyme releasing 1 µmol of glucose equivalent per min.
  1) 100 µl enzyme+100 µl of 1% PGA (polygalacturonic acid)
  2) Incubate for 10 min at 50° C.
  3) Add 400 µl DNS and boil tubes for 5 min
  4) Measure absorbance at 540 nm
  Standard curve was determined using galacturonic acid (Sigma).

α-Amylase:
  One unit is defined as the amount of enzyme that liberates 1 µmol of glucose per min.
  1) 400 µl buffer+1 ml of soluble starch (0.5%, w/w)+600 µl of diluted enzyme
  2) Incubate for 30 min at 50° C.
  3) Stop reaction by boiling for 5 min
  4) Measure glucose conc. by HPLC α-Arabinofuranosidase:
  Hydrolysis of pNP-substrate is determined by the release of p-nitrophenol and the optical density was measured at 410 nm. One enzyme unit is defined as the amount of enzyme releasing 1 µmol of p-nitrophenol per min.
  1) 100 µl of enzyme+400 µl of 10 mM p-NP-α-L-arabinofuranoside (Sigma)
  2) Incubate for 15 min at 50° C.
  3) 1 ml of cold 1M sodium carbonate was added to stop the reaction
  4) Measure absorbance at 410 nm.

Ferulic Acid Esterase:
  FAE activity was determined by measuring the ferulic acid released from methyl ferulate (Alfa Aesar). One unit is defined as the amount of enzyme that liberates 1 µmol of ferulic acid per min.
  1) Add 760 µl of buffer to tube.
  2) Add 20 µl of 100 mM MeFe (Methyl-Felulate) stock prepared in 50% (v/v) DMSO.
  3) Add 20 µl of diluted enzyme
  4) Incubate for 30 min and then add 50 µl of 20% formic acid to stop reaction.
  5) The felulic acid concentration released from MeFe was measured by HPLC.

p-Coumaryl Esterase:
  The procedure is the same with that of FAE.
  1) Add 760 µl of buffer to microfuge tube.
  2) Add 20 µl of 100 mM Methyl-coumarate stock prepared in 50% (v/v) DMSO.
  3) Add 20 µl of diluted enzyme
  4) Incubate for 30 min and then add 50 µl of 20% formic acid to stop reaction.
  5) The coumaric acid concentration released from Methyl-coumarate (Frinton Laboratories) was measured by HPLC.

Preparation of Kernels.

Corn kernels, for example yellow #2 dent corn, having a moisture content between about 10% and about 20% moisture were either tip-cap removed by a laboratory scalpel or cracked in halves using a degerminator prior to all enzymatic treatments. The degerminator mill resembled a Beall 00 size degerminator and is described in Kirleis, A. W., and Stroshine, R. L. 1990. Effects of hardness and drying air temperature on breakage susceptibility and dry-milling characteristics of yellow dent corn. Cereal Chem. 67:523-528. This was done to expose internal surface for enzymes to act on to facilitate the enzymatic deconstruction process. The degerminator was set to minimize the excessive grinding of kernels. In another embodiment, the corn kernels are mechanically fractured into particles having a mass from about 0.02 to about 0.4 g. In one embodiment, particalizing corn kernels in this manner gave from about two to about twenty corn kernel particles per corn kernels having a mass from about 0.02 g to about 0.4 g. In another embodiment, mechanically fracturing corn kernels gave from about two to about ten corn kernel particles per corn kernel.

Enzyme Screening.

Corn kernels with tip-caps removed were mixed in about pH 5.0 sodium citrate buffer at 15% w/v slurry with initial liquid volume fixed at 10 mL. Enzymes were added at 5% wt of dry corn kernels. Hydrolysis was carried out in a shaking incubator at 200 rpm, 50° C., for 1 week. All hydrolysis runs contained 1 g/L sodium azide to prevent microbial contamination.

Enzymatic Deconstruction.

Corn kernels either tip-caps removed or cracked by a degerminator were mixed in about pH 5.5 sodium citrate buffer at 25-30% w/v slurry. Two different enzyme formulations were used for the hydrolysis. In one embodiment, enzymatic digestion was affected by a mixture of enzymes which consisted of Pectinase 162L at 2% v/v, Depol 793L at 0.5% v/v, and Spezyme CP at 0.5% v/v and hydrolyzed for 24 hr or 2 weeks. The second formulation, used for obtaining a complete mass balance of fractionated kernels, included 5% v/v Pectinase 162L and 0.5% v/v Spezyme CP. Hydrolysis runs were carried out in about pH 5.5 sodium citrate buffer at 45° C., with continuous agitation at 100 rpm. Suitable agitation conditions include continuous agitation, as well as periodically agitating the aqueous enzyme solution. Time course samples were collected at 3 hrs, 6 hrs, 24 hrs, 48 hrs, and 72 hrs while the mass balance experiments were left undisturbed for the entire 72 hour hydrolysis time.

In another embodiment, suitable enzymes for use in the present invention also includes, but is not limited to, cellulases, β-glucosidases, xylanases, α-arbinofuranosidases, β-xylosidases, α-galactosidases, feruloyl esterases, and p-coumaroyl esterases.

In another embodiment, the aqueous enzyme solution is reused or recycled after collection of the solid starch product.

Fractionation.

The separation procedure for the fractionated components of cracked corn kernel hydrolysate for mass balance determination is described below. The first step involved removing the pericarp fraction upper fraction, germ, tip cap, and germ-attaching fiber residues that were floating at the surface or just below with tweezers and a spatula. Next the remaining intermediate liquid slurry was passed through a 20 mesh screen to collect the fiber fraction while most of the starch and gluten went through with the liquid. The fiber was pressed against the screen to remove as much of the liquid as possible. Liquid was distributed into 6×50 ml centrifuge tubes and spun down at 7000 rpm for 15 minutes. Following centrifugation the clear liquid was set aside and the collected volume recorded. At the bottom of the centrifuge tubes the white starch corn fraction could be seen as a lower fraction. At the top of the centrifuged liquid dark yellow residue was separated, which was removed via spatula and placed on Whatman #1 filter paper. The starch was washed with a total of 600 ml hot DI water, 6×50 ml centrifuge tubes washed twice with 50 ml hot DI water. The wash water was decanted and the starch was placed into a weigh boat and then into a 45° C. oven. Work then continued on the fiber fraction collected on the 20 mesh screen as it was removed and placed into 2×250 ml Nalgene widemouth polypropylene bottles. Hot DI water was added, 200 ml, and the bottles were shaken to dislodge any remaining starch and gluten particles. The slurry was then poured through the 20 mesh screen and the filtrate was collected for the recovery of residual starch and gluten. This procedure step was repeated twice and the filtrate was divided up into 6×50 ml centrifuge tubes and spun down at 7000 rpm for 15 minutes to obtain the solid corn starch. Starch was resuspended using a small amount of DI water. The starch was washed with hot DI water as in the previous step and the recovered starch was added to that already in the weigh boat drying at 45° C.

In other embodiments, the separation of the upper solid corn pericarp fraction, the intermediate liquid fraction, and the lower solid corn starch fraction is performed by gravity filtration. In still other embodiments, the separation is performed by centrifugal filtration. In yet other embodiments, the separation is performed by centrifugation, settling, and floatation.

Compositional Analysis.

Each fraction was tested when appropriate for monosaccharides, oligosaccharides, starch, oil, and protein using the following procedures. The liquid fraction was analyzed for monosaccharides using a BioRad HPX87-H analytical chromatography column connected to a Waters e2695 Alliance HPLC system. Oligosaccharide content was measured via NREL's LAP-14 acid hydrolysis procedure. Hydrolysate samples were analyzed on the HPLC column and system mentioned above.

Oil content was determined by extracting samples with hexane. For liquid samples, 25 ml of liquid sample was extracted with 2×25 ml volumes of n-Hexane using a separatory funnel. For solid samples, oil content was measured by extracting a one gram dry sample of 40 mesh ground solids with 2×7 ml portions of hexane in a 15 ml centrifuge tube. The organic phase was decanted into a weigh boat and allowed to evaporate in the hood leaving the extract behind to be measured by difference.

Protein in the liquid was measured using the Pierce BCA Protein Assay Kit, product #23225, obtained from Thermo Scientific. Protein in the solids samples was measured by Micro-Kjeldahl nitrogen analysis to obtain protein content.

Starch was measured in the liquid using a Megazyme Total Starch Assay Procedure kit, K-TSTA, which follows AOAC method 996.1 and AACC method 76.13 with improvements.

Results:

Corn is composed of four main components, endosperm (83% db of kernels), germ (11%), bran coat (5.3%) and tip cap (0.8%). Typical composition of yellow dent corn kernels is given in Table 1. Endosperm is approximately 88% starch embedded in a matrix of protein (8%) and fiber (2%). Bran coat and tip cap are 80-87% fiber (cellulose, hemicellulose) (www. Bungenorthamerica.com). Bran coat is composed of pericarp and seed coat layer. Interfacing endosperm and bran coat is aleurone cell layer. Pericarp and aleurone layers contain fiber (3-4%), phytosterols and fatty esters Singh, V., Moreau, R. A. and Cooke, P. H. 2001. Effect of corn milling practices on aleurone layer cells and their unique phytosterols. Cereal Chem. 78:436-441. Arabinoxylan in bran coat and aleurone layer is mainly composed of xylan backbone which is highly substituted and cross-linked by ferulate and diferulate. Efficient hydrolysis of arabinoxylan in bran coat and aleurone layer requires action of complex mixture of enzymes activities.

Table 1. Composition of corn kernels adapted from Gulati M. Kohlmann K., Ladisch. M. R. Hespell R, Bothast R. J. (1996) Assessment of ethanol production options for corn products. Bioresource Technol 58(3):253-264.

| Components in corn kernels | % by dry mass |
|---|---|
| Starch | 71.7 |
| Soluble sugars | 2.6 |
| Hemicellulose | 5.5 |
| Cellulose | 2.4 |
| Lignin | 0.2 |
| Lipids | 4.3 |
| Proteins | 10.3 |
| Ash | 1.4 |
| Balance | 1.6 |
| Total | 100 |

To effectively attack pericarp and expose endosperm for release of starch granules from kernels, pericarp and aleurone layer degrading enzymes are needed, which include cellulase, xylanase, feruroyl esterase, arabinofuranosidase, and proteases. Cellulase hydrolyzes cellulose in pericarp and endosperm fiber, makes cellulose chains shorter into shorter sugar oligomers and glucose. Xylanase, feruroyl and p-coumaroyl esterase, and arabinofuranosidase hydrolyze heteroxylans in corn pericarp and aleurone layer. Protease assists the process by hydrolyzing protein matrix in corn endosperm.

Previous work has shown that hydrolysis of dried distillers' grain fibers using 15 FPU of Spezyme CP plus 40 IU Novozyme 188 per g of glucan resulted in 90% of glucose yield within 24 hours. Kim, Y., R. Hendrickson, N. S. Mosier, M. R. Ladisch, B. Bals, V. Balan, B. E. Dale, "Enzyme Hydrolysis and Ethanol Fermentation of Liquid Hot Water and AFEX Pretreated Distillers' Grains at High-Solids Loadings," Bioresource Technology J., 99(12), 5206-5215 (2008). The work has shown that the pericarp (fiber) fraction of corn kernels is readily hydrolysable by the action of cellulase. Addition of hemicellulase, xylanase, pectinase or a mixture of these enzymes will further facilitate the de-huffing process.

Table 2 gives measured activities of various commercial enzymes we measured. Spezyme CP contains mainly cellulase and xylanase activities. Depol 692L, 793L and pectinase preparations are mainly pectinase activities with significant arabinofuranosidase, feruloyl esterase, and p-coumaroyl esterase activities required for breakdown of arabinoxylan in corn pericarp. Depol 740L is a commercial feruloyl esterase preparation with minimal side activities. These enzyme preparations were chosen due to their broad spectrum of enzyme activities and their common optimal pH and temperature ranges. To screen for enzyme formulation that gives the most solubilization of corn kernel endosperm, hydrolysis runs were conducted at about pH 5.5 sodium citrate buffer at about 45° C. After 1 week of hydrolysis the slurry was poured off and liquid was analyzed for sugar concentrations (total solubilized glucose and glucooligomers from starch and cellulose) and the remaining solids were dried in an oven at about 145° C. overnight to determine percent solubilization. The experiments were designed to quickly screen for enzymes that contain balanced enzyme activities to deconstruct kernels into their composing components rather than to obtain complete fractionation of kernels. The results of the enzyme screening hydrolysis runs are presented in FIG. 4.

Figure 7:
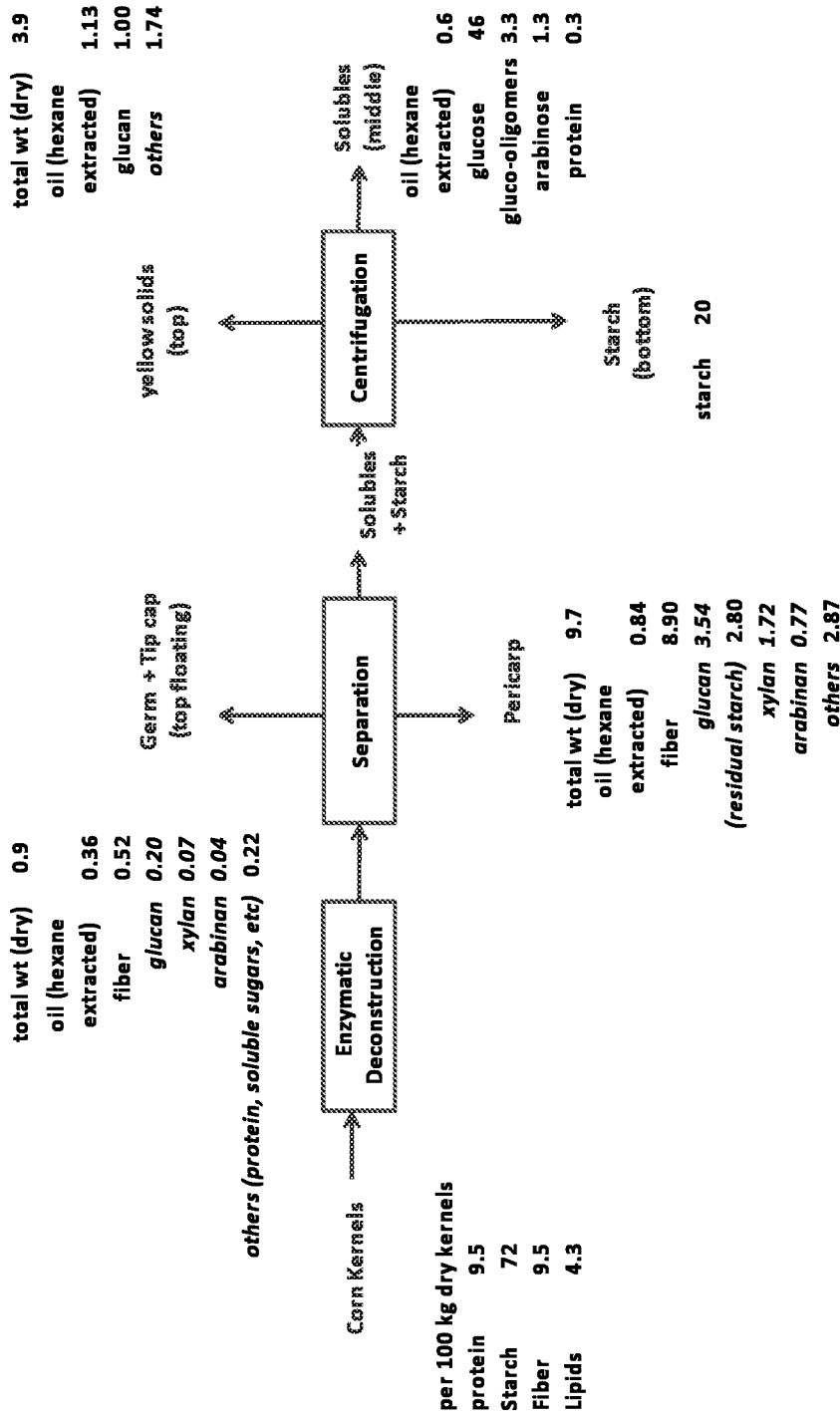
FIG. 7 shows the observed material balance of enzymatic deconstruction of cracked corn kernels, as described in the Experimental below. The experiment was performed using a 25% w/v cracked corn kernels in an aqueous slurry, 5% v/v Pectinase 162L and 0.5% Spezyme CP, pH about 5.5 citrate buffer, 45° C., 72 hrs, 100 rpm.

Spezyme CP for 72 hrs to obtain a complete mass balance of the fractionated components. The overall process flow diagram and material balance is given in FIG. 7 and summarized in Tables 3 and 4. In this regard, it will be understood that in additional embodiments herein, the mass balance of the fraction components identified in FIG. 7 or Tables 3 and/or 4, or in the discussions below, may vary from those particular numbers stated, and yet at least some amount of each of the components identified for each of the fractions will be included in the respective fractions.

As shown, the enzymatic deconstruction of corn kernels resulted in five different fractions: germs and tip cap, pericarp and some residual starch, yellow solids which were recovered as a top layer after centrifugation of liquid fraction of the slurry, starch and glucose and gluco-oligomers in

TABLE 2

Measured enzyme activities of different commercial enzymes

| Enzyme | Optimum as specified by manufacturer | protein conc. (mg/ml) by BCA | CEL (FPU/ml) | EG (CMCase, U/ml) | β-G (CBU/ml) | Xyl (OSX/ml) | β-X (U/ml) | PEC (U/ml) | α-Am (U/ml) | α-Af (U/ml) | FAE (U/ml) | p-CE (U/ml) |
|---|---|---|---|---|---|---|---|---|---|---|---|---|
| Spezyme CP | pH 4.5-5, 50° C. | 82 | 50 | nm | 128 | 2622 | 7.3 | nd | nd | 22.6 | nd | Nd |
| Depol 692L | pH 4-6, 50-65° C. | 115.8 | 5.9 | 44 | 11 | 1,510 | 18.2 | 354.5 | 38.7 | 102.2 | 0.5 | 0.9 |
| Depol 740L | pH 4-6, 40-65° C. | 29.2 | 0.1 | 0.6 | 9.1 | 88.5 | 30.3 | 9.9 | nd | 7.4 | 4.3 | 5.5 |
| Depol 793L | pH 4-7, 30-60° C. | 156.9 | 13.5 | 51.9 | 15.4 | 476 | 3.0 | 2050.3 | 49.3 | 100.7 | 0.1 | 0.3 |
| Pectinase 162L | pH 3.0-5.5, 35-45° C. | 124.8 | 24.6 | 72.4 | 90.5 | 120 | 7.3 | 2817.9 | 149.7 | 152.7 | 1.0 | 1.4 |
| Pectinase 656L | pH 3.5-5.0, 22-55° C. | 36.2 | 0.03 | 1.5 | 92.3 | 71.3 | 6.5 | 2507.1 | 244.4 | 129.8 | 1.1 | 0.7 |

CEL: Cellulase; β-G: beta-glucosidase; XYL: xylanase; β-X: beta-xylosidase; PEC: pectinase, α-Am: alpha-amylase; α-AF: alpha-arabinofuranosidase; FAE: ferulic acid esterase; p-CE: para-coumaroyl esterase. nm: not measured, nd: not detected Spezyme CP which is mainly cellulase and xylanase without significant activities that can hydrolyze branches and substituted groups of arabinoxylan only released 15% of total glucan and solubilized 15% of the initial dry mass. At the end of the 1 week hydrolysis the kernels with Spezyme CP looked still intact without significant visual disintegration. Depol 740L which lacks cellulose and xylan hydrolyzing activities but with the most amount of feruloyl esterase activity among the tested enzymes resulted in less than 10% glucan and total solids solubilization. Visually significant hollowing out of kernels was observed with Depol 692L or 793L, resulting in 20-25% of initial starch and cellulose being released from the kernels into the solution. The most enzymatic disintegration of kernels was observed with addition of either Pectinase 162L or 656L. These two enzymes, as compared to other preparations, contained more balanced enzyme activities for hydrolysis of arabinoxylan of pericarp and aleurone layer. Also, these two enzymes contained amylase activity which might have helped on solubilizing endosperm of the kernels. Visually, both pectinase 162L and 656L resulted about 40-45% endosperm being solubilized while leaving bran coat intact. However, germs were intact only with pectinase 656L while all other enzymes solubilized germs into soluble fatty acids and oils. Although we did not measure lipase activities, it appeared that these enzyme preparations except for pectinase 656L contain also germ-hydrolyzing enzyme activities.

Example 2

Material Balance

Cracked corn kernels at 25% wt/vol slurry were hydrolyzed for 72 hrs using 5% v/v Pectinase 162L and 0.5% the liquid phase. The germ and tip cap fraction was mainly fiber from tip cap and germ-attached pericarp as well as oil extractable by hexane. Oil recovery in the germ and tip cap fraction was only roughly 10% of the inlet lipids, suggesting that majority of germ is solubilized into oils and lipids which are recoverable in the liquid phase. Oil and protein mass balance was not complete due to the limitation of analytical procedures applied in this study. The yellow layer obtained after the centrifugation of liquid fraction of hydrolysate was mainly hexane extractives, glucan, and other components. Further analysis is being carried out to identify the components in the liquid slurry stream.

Figure 6:
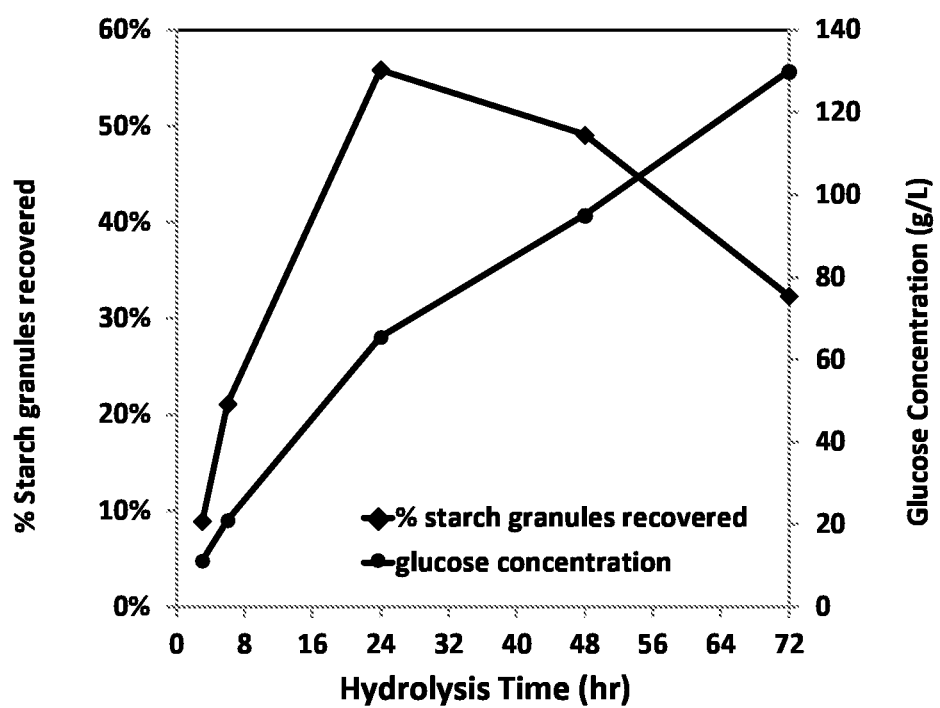
FIG. 6 depicts the enzymatic hydrolysis over time showing % starch granules recovered and glucose concentration during enzymatic deconstruction of cracked corn kernels. The experiment was performed using 25% w/v cracked corn kernels in an aqueous slurry, 5% v/v Pectinase 162L and 0.5% Spezyme CP, pH about 5.5 citrate buffer, 45° C., 72 hrs, 100 rpm.

Approximately 30% by weight of initial starch was recovered as granular starch after 72 hr. The remaining starch (60% by weight of initial) was hydrolyzed to glucose and gluco-oligomers due to amylase and gluco-amylase activities found in the enzyme preparation. Nearly all initial fiber (pericarp) was recovered. Compositions of corn pericarp (unprocessed) and the recovered pericarp from enzymatic deconstruction are given for comparison in Table 4. As shown in Table 4, the recovered pericarp from enzymatic processing was similar to the initial pericarp. The fractionated solid starch fraction was >90% pure starch as measured by starch assay. Time course of percent starch recovered as starch granules and glucose concentration is given in FIG. 6. The maximal starch recovery was achieved after 24 hr hydrolysis and continuing the hydrolysis hydrolyzed the released starch into glucose. As much as 55% starch granules were recoverable. It seems, to maximize starch granules recovery, hydrolysis time should be reduced. However, this would result in more starch being still attached to pericarp and reduce the purity of the pericarp recovered.

TABLE 3

Summary of material balance of cracked corn kernels before and after enzymatic deconstruction.

| | inlet | outlet |
|---|---|---|
| starch | 71.7 (as starch) | 20.5 (as starch) |
| | | 49.2 (as glucose + gluco-oligomers) |
| fiber (cellulose + hemicellulose) | 9.5 | 9.42 |
| lipids | 4.3 | 2.96 |
| others (protein, etc) | 9.5 | 5.10 |
| sum | 95 | 87.17 |

TABLE 4

Compositions of corn pericarp before and after enzymatic deconstruction.

| | Corn pericarp (initial) | Corn skin obtained from enzymatic deconstruction |
|---|---|---|
| Glucan | 19.2% | 21.5% |
| Xylan/Galactan | 33.9% | 32.9% |
| Arabinan | 15.0% | 14.6% |
| Acetyl | 3.4% | 2.9% |
| Acid Insoluble Residue | 5.8% | 8.4% |
| Acid Soluble Lignin | 4.2% | 4.5% |
| Ash | 0.2% | 0.2% |
| Protein | 3.4% | 3.3% |
| Mass Balance | 85.1% | 88.3% |

The uses of the terms "a" and "an" and "the" and similar references in the context of describing the invention, especially in the context of the following claims, are to be construed to cover both the singular and the plural unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and the foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method for processing a corn product, comprising: enzymatically digesting whole corn kernels or corn kernel particles in a liquid digestion medium comprising enzymes including a protease and a cellulase, to thereby separate components of the whole corn kernels or corn kernel particles by action of the digestion medium and form, by action of the digestion medium, a solid corn starch fraction including released corn starch granules, a solid pericarp fraction, and a liquid fraction containing dissolved glucose; and
separating the solid corn starch fraction from the solid pericarp fraction and from the liquid fraction so as to provide a separated solid corn starch fraction.

2. The method of claim 1, comprising enzymatically digesting corn kernel particles, and wherein the average per particle weight of the corn kernel particles is about 0.02 g to about 0.4 g.

3. The method of claim 2, also comprising:
mechanically fracturing corn kernels having a moisture content of 30% or less to form the corn kernel particles.

4. The method of claim 3, wherein the mechanically fracturing fractures each corn kernel to form, on average, two to twenty corn kernel particles having a per particle weight in the range of about 0.02 g to about 0.4 g.

5. The method of claim 2, wherein the separated solid corn starch fraction constitutes at least about 20% of the total corn starch content of the corn kernel particles.

6. The method of claim 1, wherein the separated solid corn starch fraction is constituted at least about 80% by weight of corn starch on a dry weight basis.

7. The method of claim 1, wherein the enzymatically digesting step hydrolyzes a portion of the total corn starch content of the corn kernel particles to form glucose.

8. The method of claim 7, wherein the enzymatically digesting step solubilizes a portion of a total germ content of the corn kernel particles in the liquid fraction.

9. The method of claim 1, wherein the enzymatically digesting step also forms a solid corn germ fraction, and wherein said separating the solid corn starch fraction also comprises separating the solid germ fraction from the solid corn starch fraction.

10. The method of claim 1, also comprising treating the separated solid corn starch fraction to form glucose.

11. The method of claim 10, also comprising chemically reacting the glucose in the presence of a catalyst to form a reaction product other than glucose.

12. The method of claim 1, also comprising periodically or continuously agitating the digestion medium during the enzymatically digesting step.

13. The method of claim 12, wherein the enzymatically digesting step is conducted in a vessel, and wherein the agitating comprises circulating liquid of the aqueous liquid composition through a circulation loop, the circulation loop including one or more openings into the vessel from which circulated liquid is forced sufficiently to agitate solids of the digestion medium.

14. The method of claim 1, wherein the enzymatically digesting step is conducted under conditions wherein a digested medium is formed having the solid corn starch fraction as a lower fraction, the solid corn pericarp fraction above the solid corn starch fraction, and the liquid fraction above the solid corn pericarp fraction.

15. The method of claim 1, also comprising fermenting a medium containing glucose from the liquid fraction containing dissolved glucose.

16. The method of claim 1, wherein the enzymatically digesting step includes enzymatically digesting with a pectinase, the cellulase, and a β-glucosidase.

17. The method of claim 16, wherein the enzymatically digesting step also includes enzymatically digesting with a corn germ hydrolyzing enzyme.

18. The method of claim 1, wherein the concentration of corn kernels or corn kernel particles to liquid in the digestion medium is from about 1% to about 30% w/v.

19. The method of claim 1, wherein said enzymatically digesting step comprises enzymatically digesting degerminated corn kernel particles.

20. The method of claim 19, also comprising forming the degerminated corn kernel particles by a process including degerminating a corn kernel starting material to provide a degerminated corn kernel material, and fracturing the degerminated corn kernel material to form the degerminated corn kernel particles.

21. The method of claim 1, wherein the enzymatically digesting step comprises enzymatically digesting corn kernel particles, the method also comprising:
mechanically fracturing corn kernels having a moisture content of 30% or less to form the corn kernel particles.

22. The method of claim 21, wherein the average per particle weight of the corn kernel particles is about 0.02 g to about 0.4 g.

23. The method of claim 21, wherein the mechanically fracturing step fractures each corn kernel to form, on average, two to twenty corn kernel particles having a per particle weight in the range of about 0.02 g to about 0.4 g.

24. The method of claim 21, wherein the enzymatically digesting step also forms a solid corn germ fraction, hydrolyzes a portion of a total starch content of the corn kernel particles to form glucose, and solubilizes a portion of a total germ content of the corn kernel particles in the liquid fraction.

25. The method of claim 21, also comprising treating the solid corn starch fraction to form glucose.

26. The method of claim 25, also comprising chemically reacting the glucose in the presence of a catalyst to form a reaction product other than glucose.

27. A method for deconstruction of corn kernels, comprising:
an enzyme deconstruction of corn kernels in an aqueous medium containing enzymes, the deconstruction occurring by action of the aqueous medium containing enzymes on the corn kernels, so as to form, by action of the aqueous medium containing enzymes on the corn kernels, a solid starch precipitate including released corn starch granules.

28. The method of claim 27, wherein the enzyme deconstruction results in intact germ, starch, sugar and pericarp fractions.

29. The method of claim 27, wherein enzymes for the enzymatic deconstruction comprise a pectinase, a cellulase and a ß-glucosidase.

30. The method of claim 27, comprising:
enzymatically deconstructing corn kernels into the starch precipitate, pericarp, and germ.

31. The method of claim 27, wherein enzymes of the enzymatic deconstruction are formulated to separate pericarp from endosperm while leaving germ floating on a reaction solution at the end of the process.

32. The method of claim 31, also comprising fractionating the pericarp and germ from the starch precipitate and washing the starch precipitate to generate a starch stream.

33. The method of claim 32, also comprising hydrolyzing said starch stream into glucose by an amylase.

34. The method of claim 33, wherein the corn kernels are corn kernels with their tip cap removed, or corn kernel particles.

* * * * *